(12) United States Patent
Spadafora et al.

(10) Patent No.: US 10,507,207 B2
(45) Date of Patent: Dec. 17, 2019

(54) NON-NUCLEOSIDIC INHIBITORS OF REVERSE TRANSCRIPTASE AS ANTAGONISTS OF CELL PROLIFERATION AND INDUCERS OF CELL DIFFERENTIATION

(75) Inventors: Corrado Spadafora, Rome (IT); Patrizia Lavia, Rome (IT); Elisabetta Mattei, Rome (IT); Gugliemo Palombini, Rome (IT); Rodolfo Nello Lorenzini, Blera (IT); Clara Nervi, Rome (IT)

(73) Assignee: ISTITUTO SUPERIORE DI SANITA, Rome (IT)

( * ) Notice: Subject to any disclaimer, the term of this patent is extended or adjusted under 35 U.S.C. 154(b) by 3826 days.

(21) Appl. No.: 10/500,270

(22) PCT Filed: Dec. 23, 2002

(86) PCT No.: PCT/EP02/14727
§ 371 (c)(1),
(2), (4) Date: Jul. 25, 2005

(87) PCT Pub. No.: WO03/055493
PCT Pub. Date: Jul. 10, 2003

(65) Prior Publication Data
US 2006/0166970 A1 Jul. 27, 2006

(30) Foreign Application Priority Data

Dec. 24, 2001 (IT) .............................. RM2001A0767
Aug. 19, 2002 (IT) .............................. MI2002A1833

(51) Int. Cl.
*A61K 31/535* (2006.01)
*A61K 31/496* (2006.01)
*A61K 31/536* (2006.01)
*A61K 31/551* (2006.01)

(52) U.S. Cl.
CPC .......... *A61K 31/496* (2013.01); *A61K 31/536* (2013.01); *A61K 31/551* (2013.01)

(58) Field of Classification Search
USPC ............................................... 514/228.8, 908
See application file for complete search history.

(56) References Cited

U.S. PATENT DOCUMENTS 6,258,839 B1  7/2001  Mashava

OTHER PUBLICATIONS

Cortes et al. Cancer, (Mar. 1, 2002) vol. 94, No. 5, pp. 1492-1499.*
Ghori A. et al. Telomerase inhibition as a potential new therapy for colorectal cancer. Colorectal Disease. 2000;2(2):106-112.
Grimaudo S. et al. Selective induction of apoptosis in multidrug resistant HL60R cells by the thiazolobenzoimidazole derivative 1-(2,6-difluorophenyl)-1H,3H-thiazolo [3,4-a] benzimidazole (TBZ). Eur J Cancer. Oct. 1998;34(11):1756-63.
Lam S. et al. Hypsin, a novel thermostable ribosome-inactivating protein with antifungal and antiproliferative activities from fruiting bodies of the edible mushroom Hypsizigus marmoreus. Biochem Biophys Res Commun. Jul. 27, 2001;285(4):1071-5.
Modest G. et al. HIV and refractory anemia with excess blasts (RAEB). Am J Hematol. Aug. 2002;70(4):318-9.
Murdaca G. et al. Complete remission of AIDS/Kaposi's sarcoma after treatment with a combination of two nucleoside reverse transcriptase inhibitors and one non-nucleoside reverse transcriptase inhibitor. AIDS. Jan. 25, 2002;16(2):304-5.
Shaw A. et al. Kaposi's sarcoma regression following treatment with a triple antiretroviral regimen containing nevirapine. Int J STD AIDS. Jun. 1999;10(6):417-8.
International Search Report for International Application No. PCT/EP02/14727.

* cited by examiner

*Primary Examiner* — Shobha Kantamneni
(74) *Attorney, Agent, or Firm* — Nixon Peabody, LLP

(57) ABSTRACT

The invention refers to the use of Reverse Transcriptase (RT) inhibitor compounds for the preparation of pharmaceutical compositions to counteract the loss of cellular differentiation in tumour and non tumour pathologies, said compound being able to bind the hydrophobic pocket on the RT subunit p66. Particularly preferred for such uses are the following compounds: nevirapine, efavirenz, delavirdine, corresponding salts and/or pharmaceutically acceptable derivatives thereof.

5 Claims, 12 Drawing Sheets

A

| | | G1 | S | G2/M |
|---|---|---|---|---|
| HT29 | CTR | 66,45 | 26,9 | 6,65 |
| | NEV | 78,9 | 15,4 | 5,7 |
| MCF7 | CTR | 70,3 | 9,5 | 20,2 |
| | NEV | 85,9 | 3,9 | 10,2 |
| U343 diploid pop | CTR | 60,3 | 39,1 | 0,6 |
| | NEV | 68,5 | 30,4 | 1,1 |
| U343 aneuploid pop | CTR | 68,9 | 25,5 | 5,6 |
| | NEV | 75,9 | 22,1 | 2 |
| NIH/3T3 | CTR | 73,3 | 16,4 | 10,3 |
| | NEV | 81,1 | 11,8 | 7,1 |

B

| NIH/3T3 | HT29 | MCF7 | |
|---|---|---|---|
| −   + | −   + | −   + | cyc. D1 |
| 1   2 | 3   4 | 5   6 | actin |

FIGURE 3

NON-NUCLEOSIDIC INHIBITORS OF REVERSE TRANSCRIPTASE AS ANTAGONISTS OF CELL PROLIFERATION AND INDUCERS OF CELL DIFFERENTIATION

FIELD OF THE INVENTION

The present invention refers to non-nucleosidic inhibitors of reverse transcriptase (RT) as antagonists of cell proliferation and inducers of cell differentiation for therapeutical use in the treatment and/or prevention of proliferative and differentiation diseases such as cancer.

BACKGROUND OF THE INVENTION

Endogenous, non telomeric Reverse Transcriptase (RT) is an enzyme encoded by two classes of abundant repeated elements in all eukaryotic genomes: retrotransposons and endogenous retroviruses (di Marzo Veronese F, Copeland T D, DeVico A L, Rahman R. Oroszlari S, Gallo R C, Samgadharan M G Science (1986) 231, 1289-91—Characterization of highly immunogenic p66/p51 as the reverse transcriptase of HTLV-III/LAV; Grob P M, Wu J C, Cohen K A, Ingraham R H, Shih C K, Hargrave K D, McTague T L, Merluzzi V J AIDS Res Hum Retroviruses (1992) 8, 145-52 Nonnucleoside inhibitors of HIV-1 reverse transcriptase: nevirapine as a prototype drug). Expression of RT-coding genes is generally repressed in terminally differentiated non pathological, tissues—where it is detectable only at a basal levels—yet is highly active in the mammalian germline, embryonic tissues and tumor cells. The role played by RT in such fundamental processes as cell growth and differentiation remains to be clarified.

Nevirapine, Efavirenz and Rescriptor, also known under the commercial names of VIRAMUNE®, SUSTIVA® and RESCRIPTOR® respectively, are known as non-nucleosidic inihibitors of RT and are widely used in the therapy of AIDS as antiretroviral agents. In particular nevirapine has the following empirical formula $C_{15}H_{14}N_4O$. In its pure state it is a crystalline solid of molecular weight 266.302, with a melting point of 247-249° C. and solubility of 0.1 mg/ml in water and 5.5 mg/ml in ethanol and can be prepared according to the indications present in patent EP 429.987. Nevirapine (5,11-dihydro-11-cyclopropyl-4-methyl-6H-dipyrido-[3,2-b:2',3'-e][1,4]diazepin-6-one) is comprised in the group of compounds of the 5,11-dihydro-6H-dipyrido [3,2-b:2',3'-e][1,4]diazepines, which are known as non-nucleosidic inihibitors of RT and used in the prevention and treatment of HIV infections, as described in EP 429.987.

Efavirenz (M.W. 315.68) (-)-6-chloro-4-cyclopropylethynyl-4-trifluoromethyl-1,4,-dihydro-2H-3,1-benzoxazine-one [References herein incorporated by reference: 1.YOUNG, S. D.; BRITCHER, S. F.; TRAN, L. O.; PAYNE, L. S.; LUMMA, W. C.; LYLE, T. A.; HUFF, J. R.; ANDERSON, P. S.; OLSEN, D. B.; CARROLL, S. S.; PETTIBONE, D. J.; O'BRIEN, J. A.; BALL, R. G.; BALANI, S. K.; LIN, J. H.; LONG, W. J.; BYRNES, V. W.;EMINI, E A.; ET AL., L-743,726(DMP-266): A NOVEL, HIGHLY POTENT NONNUCLEOSIDE INHIBITOR OF THE HUMAN IMMUNODEFICIENCY VIRUS TYPE 1 REVERSE TRANSCRIPTASE. ANTIMICROB AGENTS CHEMOTHER 39(12):2602-2605 (1995)]

Rescriptor (M.W. 552.68) [1-(5-methanesulphonamido)-1H-indol-2-yl-carbonyl)-4-[3-(isopropylamino)-2-pyridinyl]piperazine] (References herein incorporated by reference: 1. ROMERO, D. L.; MORGE, R. A.; GENIN, M. J.; BILES, C.; BUSSO, M.; RESNICK, L.; ALTHAUS, I. W.; REUSSER, F.; THOMAS, R. C.; TARPLEY, W. G. BIS (HETEROARYL)PIPERZINE(BHAP) RT INHIBITORS: STRUCTURE-ACTIVITY RELATIONSHIPS OF NOVEL SUBSTITUTED INDOLE ANALOGUES AND THE IDENTIFICATION OF MONOMETHANESULFONATE (U-90152S). J MED CHEM 36(10):1505-1508 (1993).

2. ROMERO, D. L.; OLMSTED, R. A.; POEL, T. J.; MORGE, R. A.; BILES, C.; KEISER, B. J.; KOPTA, L. A.; FRIIS, J. M.; HOSLEY, J. D.; STEFANSKI, K. J.; WISHKA, D. G.; EVANS, D. B.; MORRIS, J.; STEHLE, R. G.; SHARMA, S. K.; YAGI, Y.; VOORM AN, R. L.; ADAMS, W. J.; TARPLEY, W. G. TARGETING DELAVIRDINE/ATEVIRDINE RESISTANT HIV-1: IDENTIFICATION OF (ALKYLAMINO)PIPERIDINE-CONTAINING BIS(HETEROARYL)PIPERAZINES AS BROAD SPECTRUM HIV-1 REVERSE TRANSCRIPTASE INHIBITORS. J MED CHEM 39(19):3769-3789 (1996).

Preliminary studies in our group have shown that both nevirapine and efavirenz cause an early and effective developmental arrest in early mouse embryos when added to cultures of embryos prepared in in vitro fertilization (IVF) assays. That observation first indicated that both drugs can potentiality inhibit cell proliferation and prompted us to test their effect on tumor cells.

SUMMARY OF THE INVENTION

The present invention is based on the finding that non-nucleosidic RT inhibitors promote cell differentiation concomitant with reduction of cell proliferation.

The term "inhibitor" as used herein refers to compounds that interfere with the enzymatic activity through a direct binding with RT molecules. More specifically, both nevirapine and efavirenz bind the hydrophobic pocket on the RT subunit p66, which is localized close to the catalytic site—the function of which is therefore compromised. According to this definition, and within the scope of the present invention, the commercially available compounds mentioned above, i.e. VIRAMUNE (nevirapine), SUSTIVA (efavirenz) and RESCRIPTOR (delavirdine), as well as other compounds capable of interfering with RT activity, can be used in the therapy and/or prevention of pathologies characterized by loss of cellular differentiation and uncontrolled cell growth. Hence, the object of the present invention is the use of non nucleoside compounds which display RT inhibition activity according to the above mechanism, which can be employed in preventive and/or curative therapy to counteract the loss of differentiation in de-differentiating pathologies and as antiproliferative drugs in tumour therapy. In particular, RT inhibitors antagonizing the processes of cellular proliferation and de-differentiation can be used in the therapy of human tumors, in particular epithelial tumors, mesenchymal tumors and tumors of the nervous system, including leukemias and solid tumors such as teratocarcinomas, fibro- and osteo-sarcomas, colon carcinoma, breast carcinoma, glioma and hepatoma.

Among non nucleoside RT inhibitors, the present invention explicitly includes the use of commercially available compounds which are currently used for the treatment of AIDS, which have activity as non nucleoside RT inhibitors, including their relative pharmaceutical forms. Among those, particularly preferred are: Viramune® (nevirapine) (Boehringer), Sustiva® (efavirenz) (Bristol-Myers Squibb) and Rescriptor® (delavirdine) (Agouron Pharmaceuticals).

The above cited compounds, and nevirapine as a particular example, in their commonly used and commercially available pharmaceutical forms, are proposed as examples of compounds useful for the preparation of pharmaceutical compositions to be employed in cases in which cellular differentiation and/or proliferation must be controlled, therewith differentiating and anti-tumour activity. The therapeutic effect of the molecules is to be placed in relation to their RT inhibitory capacity.

A further object of the invention is the preventive or therapeutic treatment of cell proliferation in mammals, in particular in humans, with differentiating and anti-tumour actions.

Further objects will be evident from the detailed description of the invention.

BRIEF DESCRIPTION OF THE FIGURES

FIG. 1A. Functional RT activity assay after incubation of MS2 RNA with lysates from the following human (lanes 1-9) and murine (10-22) cell types: lane 1, NB4 leukemia; lane 2, R4 leukemia; lane 3, Kasumi-1 leukemia; lane 4, HL60 leukemia; lane 5, Saos-2 osteosarcoma; lane 6, MDA-231 breast carcinoma; lane 7, MCF7 breast carcinoma; lane 8, U343 Mg glioma; lane 9, HT-29 colon carcinoma; lane 10, NIH/3T3 embryo fibroblasts; lane 11, C2C7 myoblasts; lane 12, F9 teratocarcinoma; lane 13, L929 fibrosarcoma; lane 14, control reaction with F9 lysate but no MS2 RNA; lane 15, buffer only; lane 16, no mammalian cell lysate; lane 17, no MS2 RNA nor cell lysate; lane 18, positive control reaction with commercial RT; lane 19, no MS2-specific oligos; lanes 20-22: complete reaction with F9 lysate pre-incubated with 1 (lane 20), 10 (lane 21) and 100 (lane 22) μM nevirapine. Lanes M, DNA molecular weight markers; lane 23, positive control reaction with commercial Rt. FIG. 1B. Western analysis of RT proteins (upper panels) and α-tubulin (lower panels) in WCE and nuclei. WCE were from: F9 (lane 1), NIH/3T3 (lane 2), MCF7 (lane 3), MDA-231 (lane 4), NB4 (lane 5), HL60 (lane 6) and ML2 blasts (lane 7). Nuclear extracts were from: F9 (lane 1), MCF7 (lane 2), MDA-231 (lane 3), NIH 3T3 (lane 4), HL60 (lane 5) and NB4 (lane 6).

FIG. 3A. Cell cycle analysis in control and nevirapine-exposed cells. The distribution of cell cycle phases was determined by FACS after 72 h from the beginning of nevirapine treatment. In the U343 glioma cell line, the cell cycle was separately analysed in the diploid cell fraction (representing about ⅔ of all cells) and in the remaining fraction (about ⅓) which develops aneuploidy. FIG. 3B. Western immunoblotting analysis of cyclin D1 (upper panel) in extracts from the indicated cell types, cultured for 72 h with (+, lanes 2, 4 and 6) or without (−, lanes 1, 3 and 5) nevirapine. The filter was reprobed with anti-actin antibody to control equal loading (lower panel).

FIG. 4C, 60× magnification of myotubes in A. FIG. 4D, 60× magnification of myotubes in B. FIG. 4E, 60× magnification of MHC-positive myoblasts in the field in B.

FIG. 7B: Quantitative variations in gene expression. RT-PCR products hybridized with internal oligonucleotides were quantified by densitometry. The signal ratio in nevirapine to control cultures was normalized relative to that obtained for β-actin in the same experiment. Dark histograms represent the mean value, and light histograms the standard deviation, from at least three experiments for each gene.

FIG. 8B: F9 cells). Cells were cultured with (dashed lines) and without (DMSO, solid line) efavirenz. The proliferation rate is expressed as the ratio of counted cells at the indicated times relative to the initial number of seeded cells, taken as 1. Points represent the mean value from at least three independent assays.

(FIG. 9A HeLa $1^{st}$ cycle; FIG. 9B: HeLa $2^{nd}$ cycle, FIG. 9C SAOS $1^{st}$ cycle, FIG. 9D SAOS $2^{nd}$ cycle). Cells were cultured with (dashed line) and without (DMSO, solid line) efavirenz. The proliferation rate is expressed as the ratio of counted cells at the indicated times relative to the initial number of seeded cells, taken as 1. Points represent the mean value from three independent assays.

DETAILED DESCRIPTION OF THE INVENTION

Figure 1:
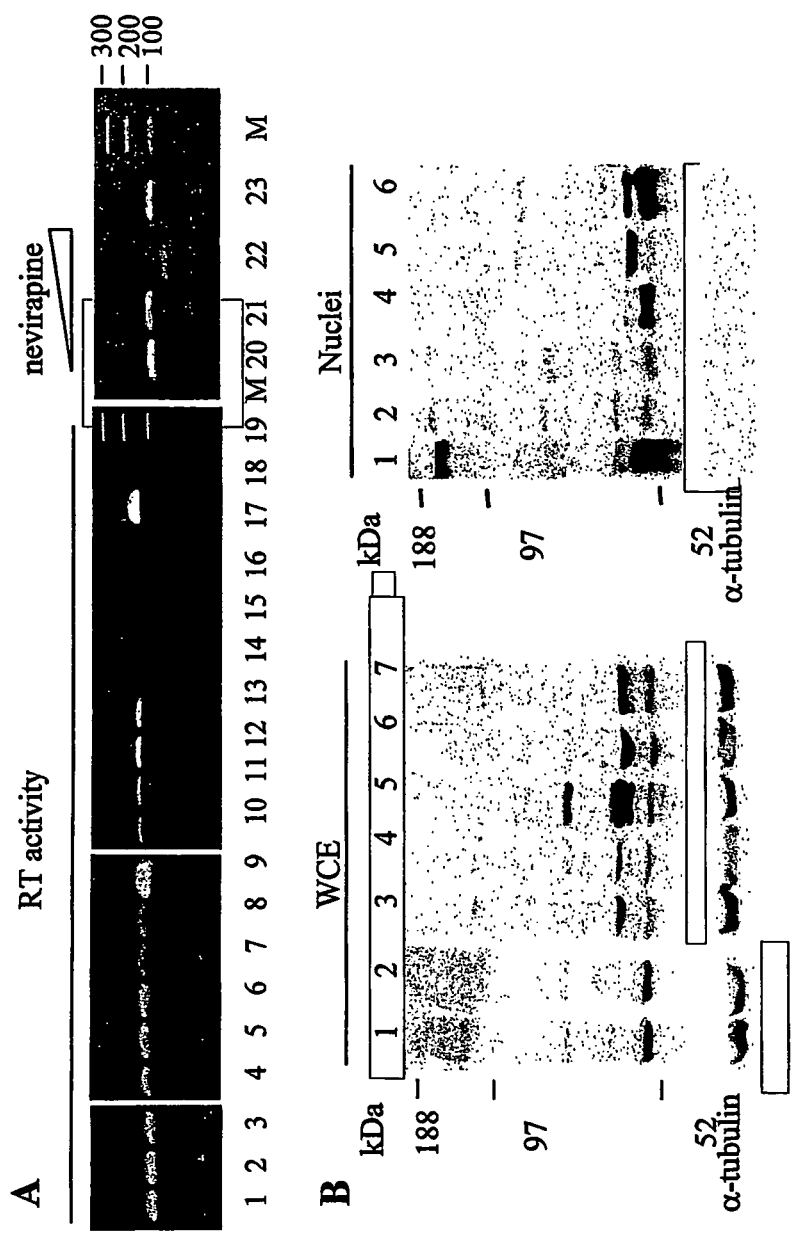
FIG. 1: Reverse transcriptase in murine and human cell lines.

We initially detected an endogenous RT activity, the enzyme targeted by inhibitors, in a variety of murine and human tumor cell line extracts using a PCR-based RT assay.

We then added 350-400 µM nevirapine, or 10-20 µM efavirenz, for several days in cultures of murine progenitor cells (i.e., C2C7 myogenic precursor cells; NIH/3T3 embryo fibroblasts) and murine and human tumorigenic cell lines (F9 teratocarcinoma; L929 fibrosarcoma; HT-29 colon carcinoma; MCF-7 breast carcinoma expressing the estrogen receptor (ER+); MDA-231 breast carcinoma, negative for ER expression (ER−); U343 Mg glioma and Saos-2 osteosarcoma). The results showed that RT inhibitors induce a decrease in the rate of cell proliferation and promote cell differentiation. Differentiation was also observed in acute myeloid leukemia (AML) cell lines (NB4, HL60, Kasumi-1) and primary blasts from two AML patients, as indicated by morphological, functional and immunophenotypic assays.

RT-PCR analysis of mRNA extracted from F9 cells before and after exposure to nevirapine depicted a substantial reprogramming of gene expression in a set of genes which critically regulate the cell cycle: cyclin D1 and D3 were down-regulated; conversely, their antagonist p16 was up-regulated; to a lesser extent, the p27 kinase inhibitor and the Rb-1 and Rb-2 retinoblastoma-related genes were also down-regulated.

These results support the view that: a) an endogenous RT activity is involved in tumorigenesis and b) RT inhibitors promote the conversion of tumor phenotypes to normal phenotypes. Nevirapine-induced differentiation was studied in greater detail in multipotent F9 and myogenic C2C7 cell lines by following up the appearance of specific differentiation markers that are not expressed in progenitor cells, i.e. collagen IV α-chain in F9 cells and myosin in C2C7 cells, respectively. Moreover, studies at the morphological (nucleo/cytoplasmic ratio and decreased basophylia), functional (NBT assay) and immunophenotypic (expression of lineage-specific surface antigens) levels indicate that nevirapine treatment can rescue the differentiation block present in human AML cell lines in primary tranformed blasts from AML patients.

Based on these findings, we propose that the non nucleoside compounds that show RT inhibition activity according to the above mechanism be used in preventive and/or curative therapy as drugs to counteract the loss of differentiation in de-differentiating pathologies such as rhabdomyosarcoma, and as antiproliferative drugs in tumour therapy, in particular epithelial tumors, mesenchymal tumors and tumors of the nervous system, including leukemias and solid tumors such as teratocarcinomas, fibro- and osteo-sarcomas, colon carcinoma, breast carcinoma, glioma and hepatoma.

Preferred are the compounds which are commercially available and used for the treatment of AIDS which have activity as non nucleoside RT inhibitors. Particularly preferred are: Viramune (nevirapine) (Boehringer), Sustiva (efavirenz) (Bristol-Meyers Squibb) and Rescriptor (delavirdine) (Agouron Pharmaceuticals).

The above cited compounds, and nevirapine as a particular example, in their commonly used and commercially available pharmaceutical forms, are proposed as examples of substances useful for the preparation of pharmaceutical compositions to be employed in cases in which differentiation must be controlled, at the same time counteracting cellular proliferation, therefore with differentiating and antitumour action. The therapeutic effect of the molecules is to be placed in relation to their RT inhibitory capacity.

The preventive or therapeutic treatment of cell proliferation according to the invention can be performed in mammals, in particular in humans.

The subjects in need can be treated with a therapeutically effective amount of at least one compound that displays activity as non nucleoside RT inhibitor and provides a therapeutic benefit to the subject.

The non nucleoside compounds according to the invention can be used in pharmaceutical compositions to prepare medicaments with differentiating and antitumour action. The composition for the uses described in the present invention may be obtained by mixing together effective quantities of at least one active principle with one or more physiologically acceptable carriers and/or diluents and/or solvents and/or excipients and auxiliaries which facilitate processing of the active compounds into preparations which can be used pharmaceutically, such as in form of pills, solutions, suspensions. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. The pharmaceutical compositions may be administered orally, or by intravenous intramuscular or hypodermic injection.

Uses, dosages and ways of administration are according to the indications present in patent EP 429.987.

The doses and modalities of administration vary according to the type and gravity of the affection.

This text will now proceed by describing some experimental examples using the above mentioned molecules. However, it is to be stressed that, owing to the different chemical structure of the compounds that are preferred according to the present invention, it will be understood that the invention is not limited to such molecules but other compounds that display activity as RT inhibitor agents may be applied as well.

The following examples are to be considered as illustrative and not limiting of the scope of the present invention.

EXAMPLE 1

Endogenous RT Activity in Tumor Cells

The RT enzymatic activity, which is the target of the inhibitors described herein, has been detected in all cell lines, of both murine and human origin, that have been tested in this work using a PCR-based assay. Results summarized in FIG. 1, A show that lysates from all cell lines harbor a RT activity able to retrotranscribe in vitro an exogenous RNA (MS2 phage RNA), generating an amplified product of the expected size, i.e. 112 bp (lanes 1-13); the cDNA is not synthesized if MS2 RNA (lane 14) or cell lysate (lane 16) are omitted in the incubation mixture. Moreover, RT activity is inhibited when cell lysate is pre-incubated with nevirapine in a dose-dependent manner: the 112 bp-product is abolished after incubation with 100 µM (lane 22) but not with 1 (lane 20) or 10 µM (lane 21). The presence of RT enzyme in tumor cells is further confirmed by Western blot analysis. FIG. 1, B shows that protein molecules are recognized by specific anti-RT polyclonal antibody, both in whole cell (WCE) and in nuclear lysates.

These results-show that RT is present in tumor cells, both as a protein and as an enzymatic activity, and that is inhibited by nevirapine.

EXAMPLE 2

Figure 2:
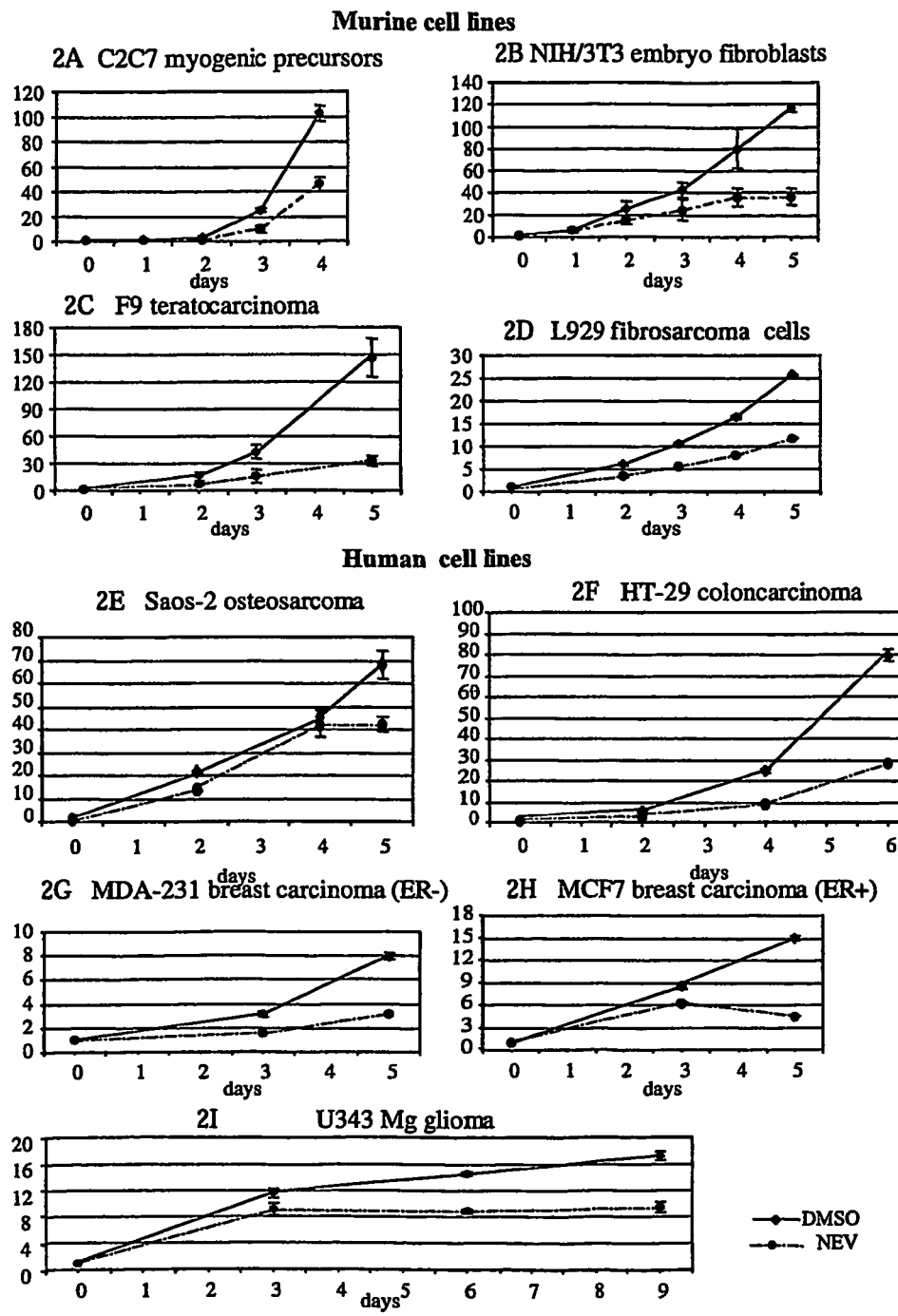
FIG. 2: Nevirapine inhibits proliferation in murine and human cell lines. Cells were cultured with (dashed line) and without (DMSO, solid line) nevirapine. The proliferation rate is expressed as the ratio of counted cells at the indicated times relative to the initial number of seeded cells, taken as 1. Points represent the mean value and bars the standard deviation from at least three independent assays for all cell types.

Incubation of Murine and Human Cell Cultures with Nevirapine: Slow-Down of Cell of Cell Doublings Murine C2C7 myogenic precursors, NIH/3T3 embryo fibroblasts, F9 teratocarcinoma and L929 fibrosarcoma cells, and human cells from the following cell lines: Saos-2 osteosarcoma, HT-29 colon carcinoma, MDA-231 breast carcinoma (ER−), MCF7 breast carcinoma (ER+), U343 glioma, were cultured in DMEM containing 10-20% fetal serum and 350 µM nevirapine diluted from a stock solution (250 mM) in 100% DMSO. Cells were plated at a density of $2\text{-}5 \times 10^4$ in 35 mm Petri dishes and exposed to nevirapine 5-6 hours later. Samples were withdrawn at specific times and cells were counted in nevirapine-exposed and control (DMSO-exposed) cultures. The results summarized in FIG. 2 show that exposure to nevirapine (broken line) decreases the rate of proliferation in all cell lines. Some cell type-specific differences were observed in the response to the suppressive effect of the drug: F9 teratocarcinoma cells showed the highest response, with a 5-fold reduction in the proliferation rate after 120 h of exposure. A comparable effectiveness was depicted in HT-29 colon carcinoma cells. Saos-2 osteosarcoma cells were the most slowly responsive type, and only after 5 days of exposure did the growth rate begin to decrease compared to control cultures.

EXAMPLE 3

Incubation of Cell Cultures with Nevirapine: Exit from Cell Cycle

FACS analysis of nevirapine-exposed cell cultures depicted changes in the cell cycle profile of several cell types: as shown in FIG. 3A, cells with a G0/G1 DNA content accumulated in NIH/3T3, HT-29, MCF-7 and U343 Mg cultures after 72 h of nevirapine treatment, whereas at these same times control samples displayed cell cycle profiles typical of proliferating cultures. This was accompanied by a substantial decrease in cyclin D1 levels in NIH/3T3, HT-29, MCF-7 (FIG. 3B), and U343 Mg glioma (data not shown) cultures exposed to nevirapine compared to non-exposed controls.

EXAMPLE 4

Incubation of Cell Cultures with Nevirapine: Induction of Differentiation

Figure 4:
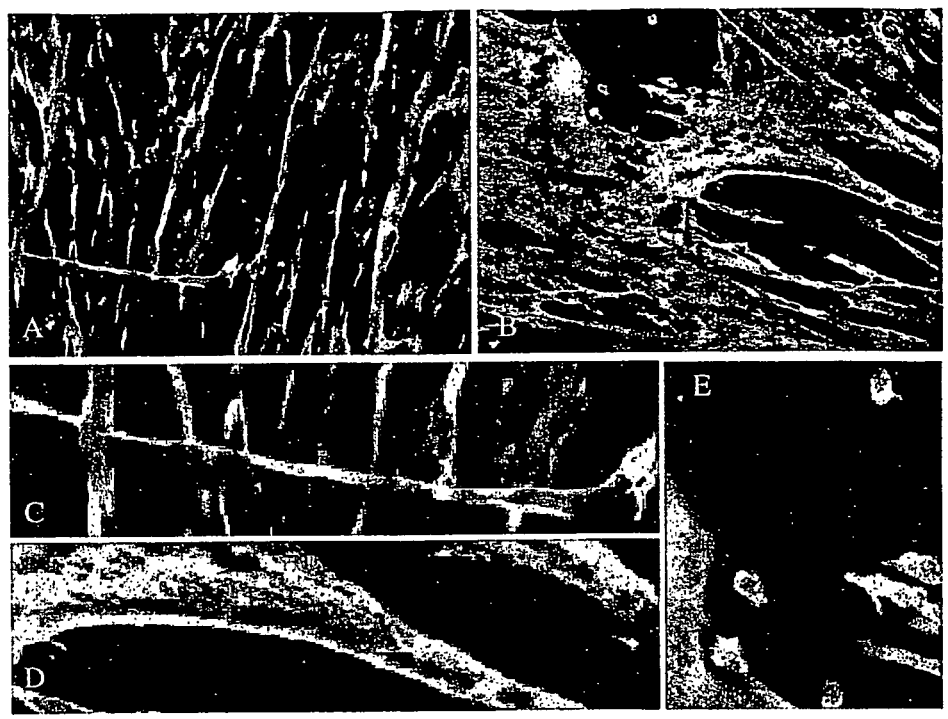
FIG. 4: Differentiation of C2C7 myogenic cells after exposure to nevirapine. C2C7 myoblasts pre-treated with DMSO (A, C) or nevirapine (B, D, E) prior to culturing in differentiation medium were stained with anti-MHC (FITC, green) and Hoechst 33258 to visualize nuclei (in blue); merged pictures are shown. At 20× magnification, myotubes in control cultures (FIG. 4A) are thinner and less frequent than after nevirapine treatment (FIG. 4B).

Nevirapine influences the process of cell differentiation as shown using model cell systems capable of undergoing differentiation in vitro with well characterized patterns. Murine C2C7 myogenic satellite cells, which proliferate as mononucleated myoblasts can be induced to differentiate upon growth factor withdrawal and form multinucleated myotubes that express muscle-specific genes. In our experiments C2C7 cells were cultured with or without nevirapine for 90 h (during which control cultures reached saturation density) and then transferred to differentiation medium for 48 h. By light-field microscopy scoring (n=300 cells from randomly selected fields), the ratio between multinucleated myotubes (i.e., cells with more than three nuclei) and mono/binucleated cells was about 1:1 in nevirapine-treated compared to 1:2 in untreated samples. Cells monolayers were further analyzed by immunofluorescence (IF) using a polyclonal antibody to myosin heavy chain (MHC), a late marker of muscle differentiation. In control cultures kept in differentiation medium for 48 h, multinucleated MHC-containing myotubes were thin and markedly smaller (FIG. 4C) than in cultures pre-treated is with nevirapine (FIG. 4D). Isolated myoblasts were mostly MHC-negative in control cultures (FIG. 4A), whereas myosin synthesis was already activated in isolated myoblasts in nevirapine-treated plates (FIG. 4E).

Figure 5:
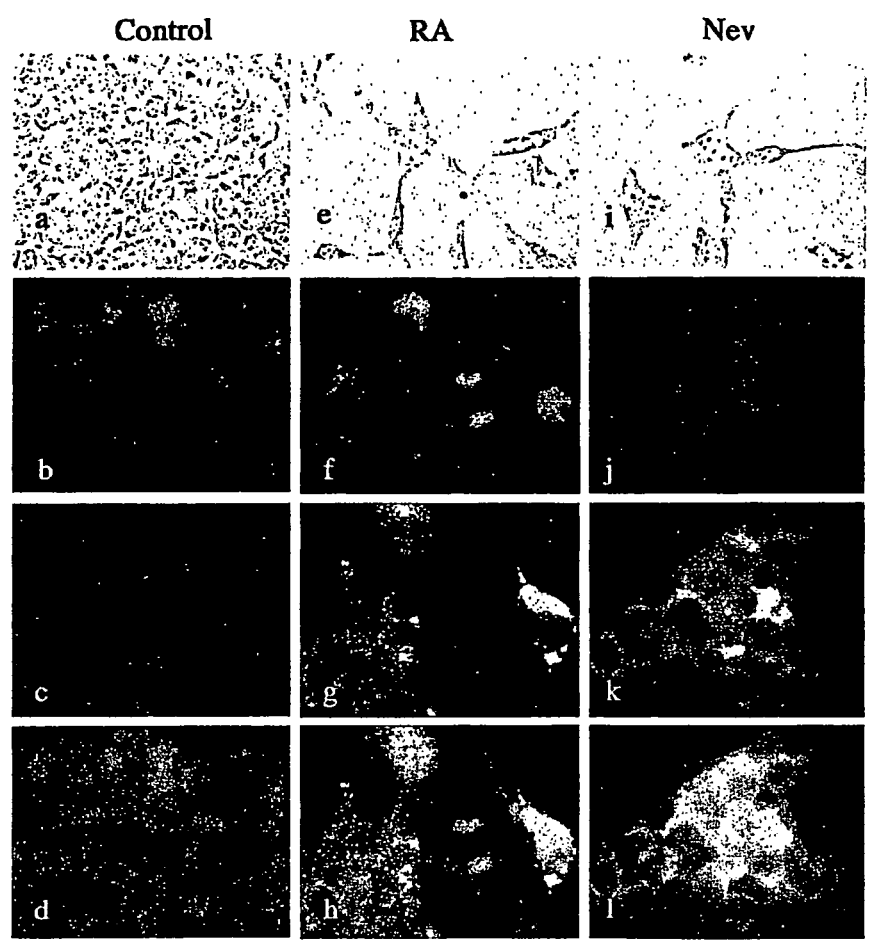
FIG. 5: Morphological differentiation in RA- and nevirapine-exposed F9 cells. F9 cultures exposed to DMSO (controls, FIG. 5a, FIG. 5b, FIG. 5c, FIG. 5d), nevirapine (FIG. 5e, FIG. 5f, FIG. 5g, FIG. 5h) or RA (FIG. 5i, FIG. 5j, FIG. 5k, FIG. 5l) were first examined in vivo after 72 h of culture to record the morphological reorganization (panels FIG. 5a, FIG. 5e, FIG. 5i, 60× objective). After 96 h, samples were fixed and processed for IF of collagen type IV (α1) chain (FIG. 5c, FIG. 5g, FIG. 5k) and DAPI staining of nuclei (FIG. 5b, FIG. 5f, FIG. 5j); pictures are merged in FIG. 5d, FIG. 5h and FIG. 5l (100× objective).

Nevirapine also triggered differentiation in teratocarcinoma F9 cells. Untreated F9 cells have a rounded shape and tend to form aggregates during growth (FIG. 5a). When exposed to retinoic acid (RA), a well known promoter of differentiation, characteristic signs of morphological differentiation become apparent after 72 h (FIG. 5e), including a decreased tendency to form aggregates, increased adhesiveness and reorganization of the cell surface with the appearance of a differentiated morphology. Similar changes were observed in nevirapine-exposed cultures (FIG. 5i). The -morphological reorganization was accompanied by an increased synthesis of collagen type IV($\alpha$1) chain (FIG. 5k), a marker of differentiation induced in response to RA (FIG. 5g), synthesized at low levels in control cultures (FIG. 5c). Together the results in FIGS. 4 and 5 indicate that nevirapine triggers or facilitates the onset of differentiation in two different cell types.

EXAMPLE 5

Figure 6:
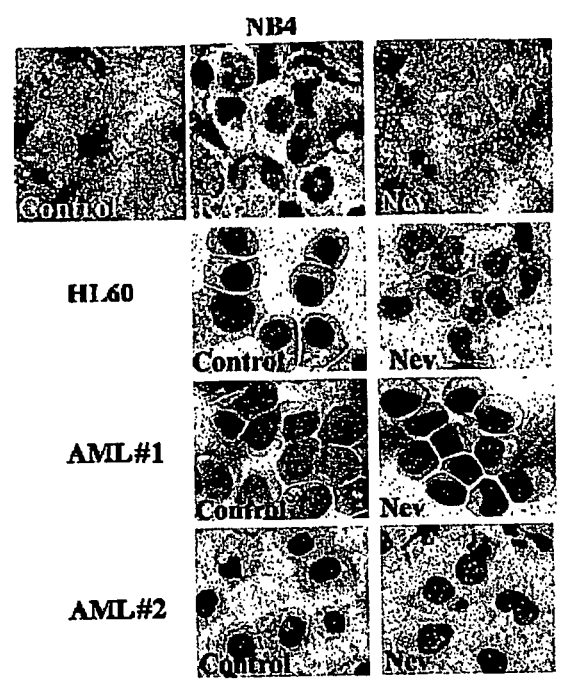
FIG. 6: Nevirapine treatment relieves the differentiation block in AML blasts. Morphological differentiation, revealed by Wright-Giemsa staining, in the promyelocytic cell line NB4; HL60 cells; and blasts from two AML patients (AML#1 and AML#2) after treatment with 400 μM nevirapine (Nev) for 5 days. NB4 cells were also treated with 1 μM RA, which induces granulocyte differentiation. Untreated cells are shown as controls.

Nevirapine Treatment Induces Human Acute Myeloid Leukemia (AML) Blast Differentiation We analyzed the effect of nevirapine in the acute promyelocytic NB4, expressing the t(15;17) oncoprotein PML/RAR, responsible for the differentiation block present in these blasts, and the acute myeloblastic leukemia HL60 cell lines, in comparison to their known sensitivity to RA-induced granulocytic differentiation. After five days of nevirapine treatment, the appearance of cells with a myelomonocytic-like morphology was evident in both cell lines (FIG. 6), whereas cells with metamyelocyte-like morphology were induced by 1 µM RA, as reported (FIG. 6 and data not shown). We then analysed the expression of the three surface antigens CD11b, CD14 and CD15, after four days of culture in the presence of RA or nevirapine (Table 1). The induction of CD11b is associated with granulocytic differentiation, CD14 is considered a monocytic specific antigen and CD15 is a myelomonocytic antigen. Simultaneous induction of CD14 and CD11b relates to monocytic differentiation. Consistent with the induction of granulocytic differentiation, RA treatment increased the levels of CD11b and CD15, but not CD14, in both cell lines. In nevirapine-treated NB4 and HL60 cells, a strong induction of expression of CD15, and, to a lesser degree, CD11b and CD14 markers was detected. Thus, nevirapine treatment induces expression of myelomonocytic differentiation markers, consistent with the morphological studies.

Nevirapine treatment also increased the number of positive cells in the NBT dye reduction assay by about 2.0-3.5 fold (Table 2).

The differentiating effect of nevirapine was further analysed in myeloid leukemia cells poorly sensitive to RA-induced granulocytic differentiation, such as the Kasumi-1 cell line expressing the t(8;21) translocation product AML1/ETO, and in primary blasts from two AML patients. Nevirapine treatment, though not actually arresting proliferation, induced a modest yet constant accumulation of cells in the G1 phase of the cell cycle (data not shown). In addition, both Kasumi-1 cells and primary AML blasts responded to nevirapine treatment by triggering differentiation, as revealed by the induction of: (i) morphological changes related to myelomonocytic differentiation (FIG. 6), consisting of chromatin condensation with initial nuclear segmentation, decreased nuclear/cytoplasmic ratio, decreased cytosolic basophilia and appearance of a paranuclear Golgi region (specific granules were evident in the case of AML#1); (ii) functional changes, indicated by increased NBT positivity (Table 2); (iii) changes in the expression of myeloid immunophenotypic markers CD11b, CD14 and CD15 (Table 1 and data not shown). The extent of induction of myeloid differentiation features in primary AML blasts was comparable to that detected in NB4 and HL60 cells. Insert Tab. 1 and Tab. 2

TABLE 1

Cytofluorimetric analysis of cell surface markers in NB4 and HL60 cell lines after exposure for 4 days to RA (1 µM) or NEV (450 µM): mean fluorescence intensity (AU) of specific markers.

| Markers | Control NB4 cells | RA | NEV | Control HL60 cells | RA | NEV | Control AML#1 | NEV |
|---|---|---|---|---|---|---|---|---|
| CD11b | 7.2 | 53.7 | 10.1 | 12.1 | 15.3 | 16.6 | 5.6 | 5.9 |
| CD14 | 18.3 | 19.1 | 23.1 | 34.3 | 23.7 | 45.3 | 8.1 | 8.8 |
| CD15 | 106.5 | 421.7 | 196.3 | 122.5 | 609.7 | 1298.1 | 5.5 | 15.6 |

TABLE 2

Effect of RA or Nev on growth and differentiation of NB4, HL60, Kasumi-1 cell lines and primary leukemia blasts from two AML patients after exposure for 4 days.

| Treatment | Viable cells $N^0 \times 10^5$ NB4 cells | NBT+ (%) | Viable cells $N^0 \times 10^5$ HL60 cells | NBT+ (%) |
|---|---|---|---|---|
| Control | 2.6 ± 0.2 | 9.1 ± 0.5 | 9.2 ± 1.8 | 13.3 ± 0.8 |
| RA (1 µM) | 1.4 ± 0.1 | 80.6 ± 4.5 | 6.5 ± 0.9 | 31.2 ± 1.4 |
| Nev (350 µM) | 2.6 ± 0.4 | 37.2 ± 1.4 | 4.7 ± 1.1 | 37.8 ± 2.5 |

| Treatment | Viable cells $N^0 \times 10^5$ Kasumi-1 cells | NBT+ (%) | Viable cells $N^0 \times 10^5$ AML #1 | NBT+ (%) | Viable cells $N^0 \times 10^5$ AML #2 | NBT (%) |
|---|---|---|---|---|---|---|
| Control | 3.3 ± 0.6 | 14.1 ± 0.5 | 0.9 ± 0.2 | 9.2 ± 0.4 | 1.8 ± 0.3 | 37.5 ± 4.9 |
| Nev(350 µM) | 4.5 ± 0.9 | 31.2 ± 1.1 | 0.6 ± 0.1 | 19.5 ± 0.7 | 1.2 ± 0.1 | 68.1 ± 1.4 |

EXAMPLE 6

Figure 7:
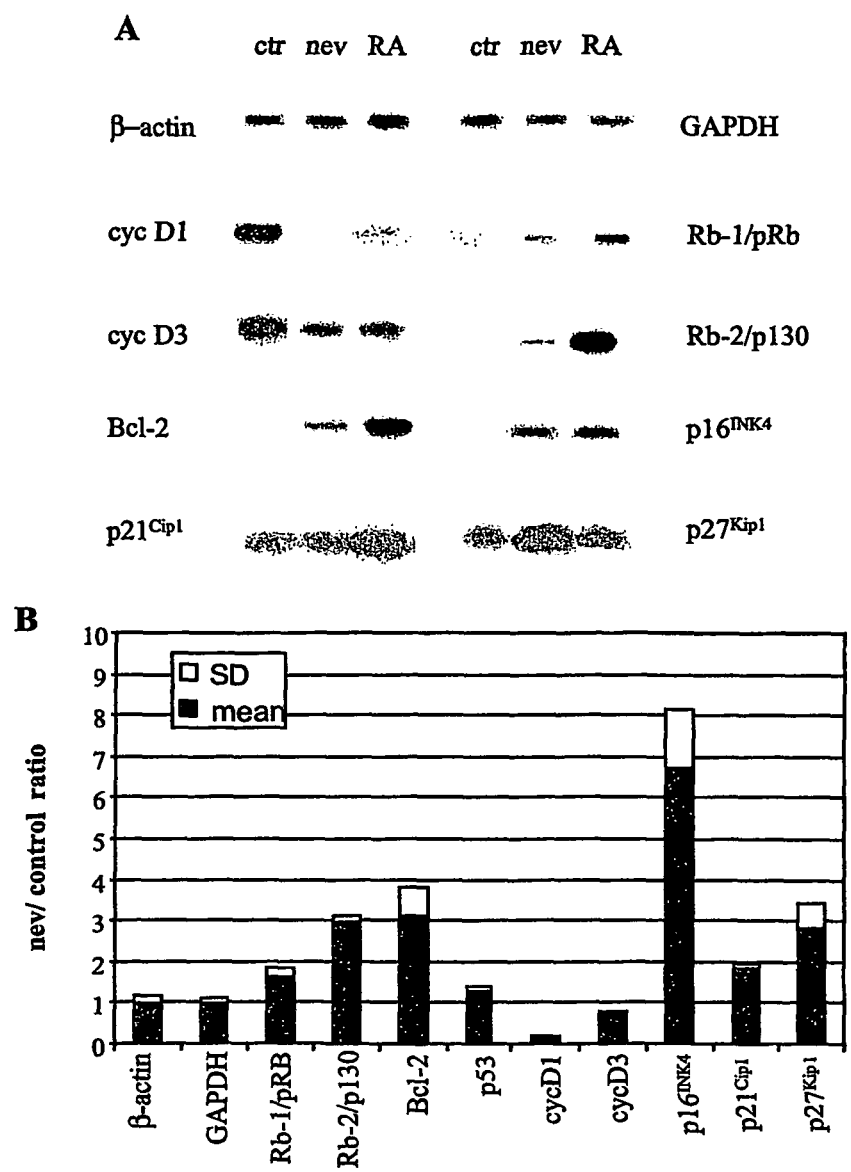
FIG. 7: Nevirapine induces variations in gene expression in F9 cells. Total RNA from F9 cells cultured with DMSO (controls), nevirapine or RA was subjected to RT-PCR amplification with oligonucleotides for the indicated genes, blotted and hybridized with internal oligonucleotides. Representative panels are shown in FIG. 7A.

Altered Expression of Cell Cycle Regulatory Genes in Nevirapine-Treated F9 Cells To assess whether the ability of nevirapine to influence growth and differentiation reflected changes in expression of specific genes, RNA was extracted from control, nevirapine- and RA-exposed F9 cells and subjected to semi-quantitative RT-PCR analysis. We examined a set of genes encoding D-type cyclins; growth inhibitors; modulators of apoptosis; and housekeeping proteins. Representative panels are shown in FIG. 7A and results are quantified in FIG. 7B. Most significant variations were recorded for the cyclin D1 gene, which was down-regulated by 7-fold, whereas p16$^{INK4a}$, encoding the major antagonist of D-type cyclins, was up-regulated by nearly 8-fold, in nevirapine compared to non-exposed F9 cultures. Up-regulation was also recorded for p27$^{Kip1}$, which critically modulates proliferation in response to cell shape and adhesion; Rb-2/p130, which is associated with withdrawal from the proliferative cycle; and Bcl-2, which can facilitate growth arrest in some cell types. Cyclin D3 expression was down-regulated in response to nevirapine. These changes are specific, because expression of housekeeping genes (β-actin, GAPDH), as well as p53, was unaffected.

EXAMPLE 7

Incubation of Murine Cell Cultures with Efavirenz: Dose Effect

Figure 8:
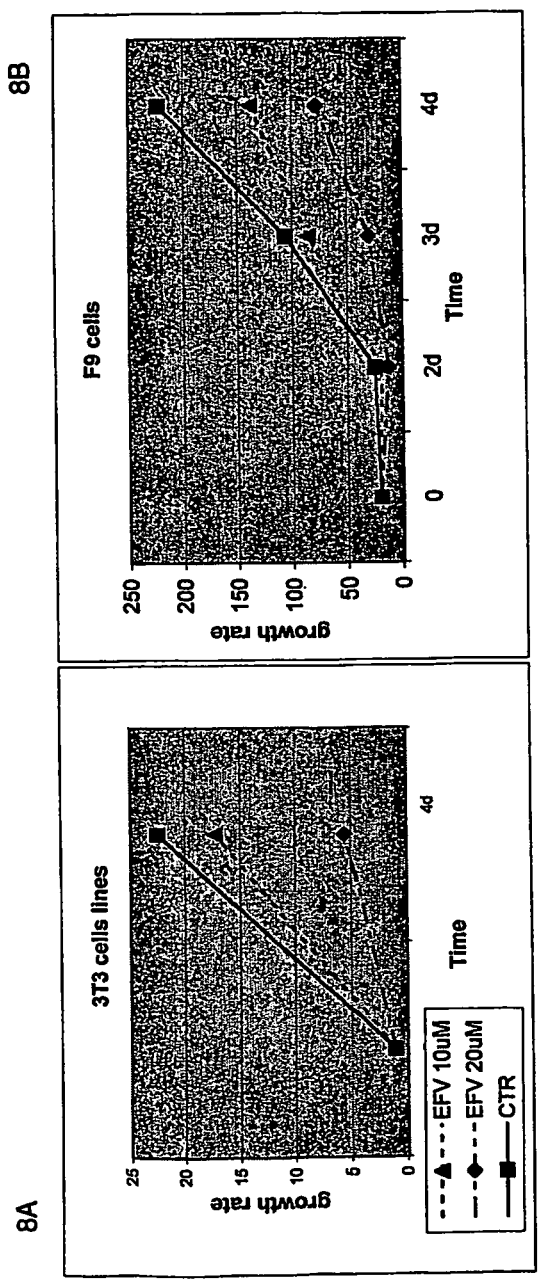
FIG. 8: Efavirenz inhibits proliferation in murine cell lines (FIG. 8A 3T3 cell lines.

NIH/3T3 embryo fibroblasts and F9 teratocarcinoma cells were cultured in DMEM containing 10-20% fetal serum and two concentrations of efavirenz, i.e. 10 and 20 µM, diluted from a stock solution (10 mM) in 100% DMSO. Cells were plated at a density of 2-5×10$^4$ in 35 mm Petri dishes and exposed to efavirenz 5-6 hours later. Samples were withdrawn at specific times and cells were counted in efavirenz-exposed compared to parallel non-exposed cell cultures. Results in FIG. 8 show that exposure to efavirenz (broken line) decreases the rate of proliferation in both cell lines in a dose-dependent manner as compared to non-exposed cells (solid line).

EXAMPLE 8

Incubation of Human Cell Cultures with Efavirenz: Time Dependency

Figure 9:
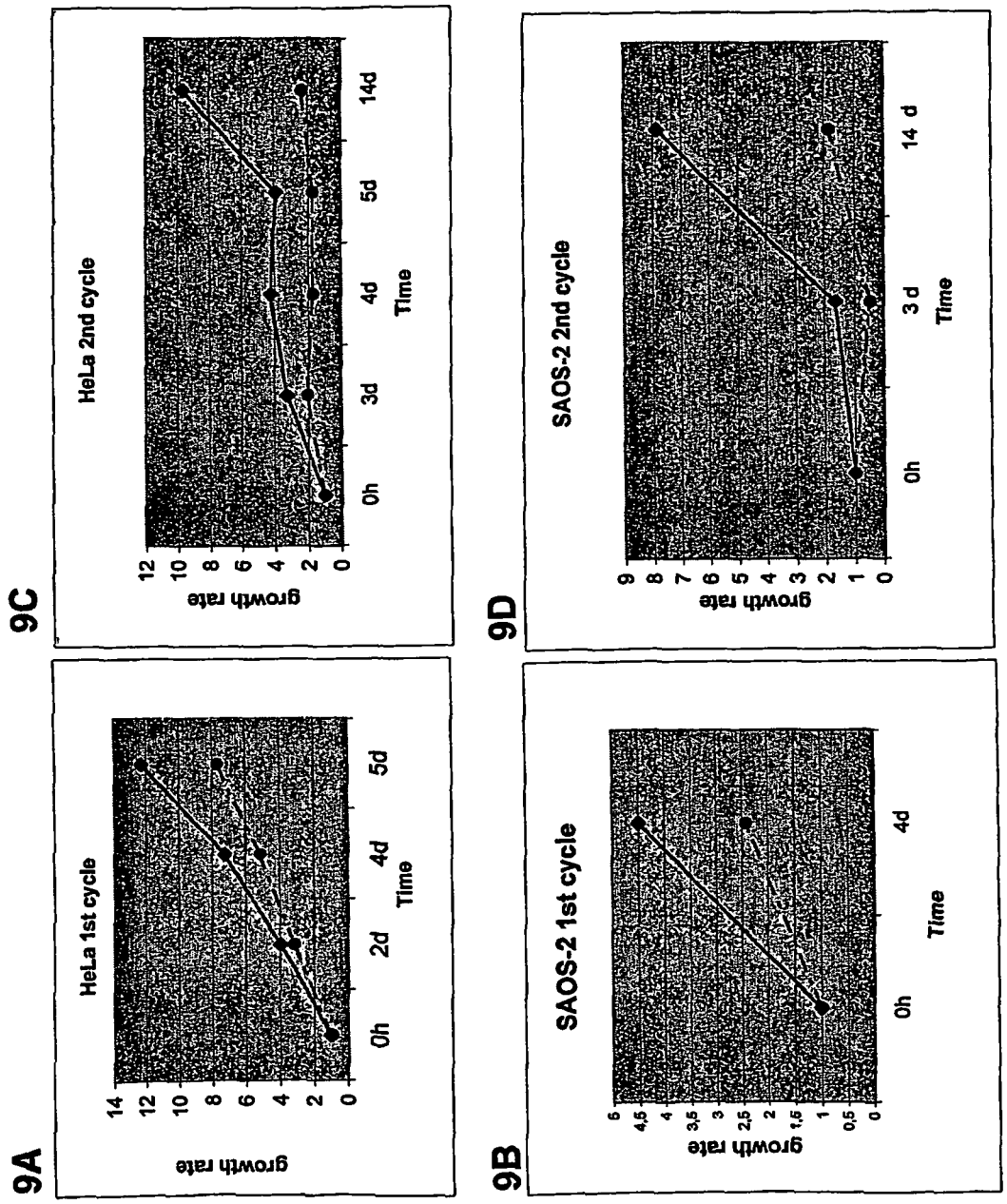
FIG. 9: Efavirenz inhibits proliferation in human cell lines.

The effect of efavirenz was further tested in human HeLa adenocarcinoma and Saos-2 osteosarcoma cells. Both cell lines were cultured in the conditions described above (Example 6). To establish if prolonged exposure to the drug improved the effectiveness of growth inhibition, both cell lines were exposed to efavirenz in two subsequent cycles: during the 1$^{st}$ cycle cells were continuously exposed to 20 µM efavirenz for 5 days; cells were then diluted, reseeded again and the 2$^{nd}$ cycle exposure was initiated the following day with fresh drug. Results in FIG. 9 show that both HeLa (panels A) and Saos-2 (panels B) cell lines were sensitive to efavirenz and underwent a significant reduction in the rate of cell growth. The inhibitory effect was time-dependent, since in both HeLa and Saos-2 cultures, the $1^{st}$ cycle of exposure (5 days) yielded a 1.6- and 1.5-fold reduction, respectively, whereas a 5- and 4-fold reduction was obtained in the $2^{nd}$ cycle (carried out until day 20 from the onset of exposure).

EXAMPLE 9

Anti-Tumor Activity of Nevirapine in vivo: Treatment of Morris 3924A Rat Hepatoma a) Rat Strain and Tumor Features Rat strain: ACI/T inbred (about 180 gr)

Tumor: Morris 3924A hepatoma is a fast-growing tumor which develops in inbred ACI/T animals. Three weeks after inoculation the tumor size is about 10 cm$^3$.

Preparation of tumor cells: hepatoma tumor cells are prepared from the animal about two weeks after inoculation. The tumor is surgically removed from the animal, separated from connective and necrotic tissues and minced in small pieces. Tumor fragments are then suspended in sterile physiological solution and inoculated in the internal site of one thigh using a 20 ml-syringe with a large size needle. Routinely 0.5 ml of cell suspension are injected. The success rate of tumor implantation is nearly 99%.

Procedures: 3 rats were pre-treated with nevirapine by injecting daily 0.2 ml/rat of nevirapine solution (stock solution=180 mg/2 ml DMSO) for 11 days (18 mg/rat/day). On the eleventh day, hepatoma cells were inoculated subcutaneously in pre-treated and in three non-treated control rats.

Figure 10:
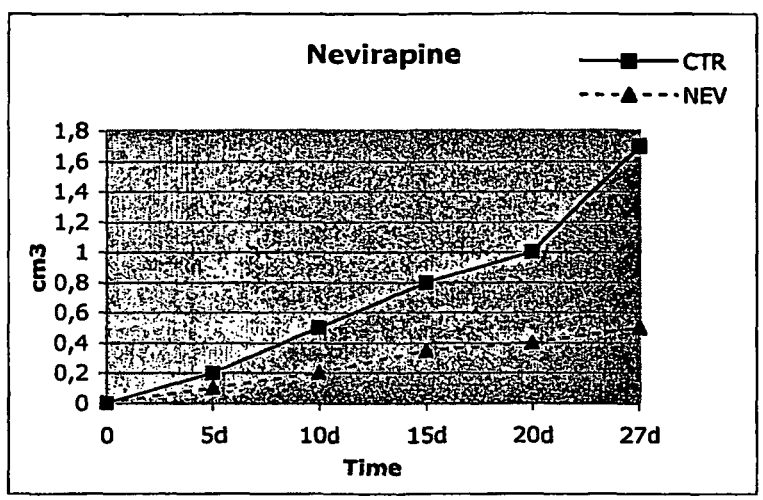
FIG. 10: Morris hepatoma growth in control (solid line) and nevirapine-treated rats (broken line). The rate of tumor growth is expressed as the volume (in $cm^3$) over time (in days from the time of inoculation).
Figure 11:
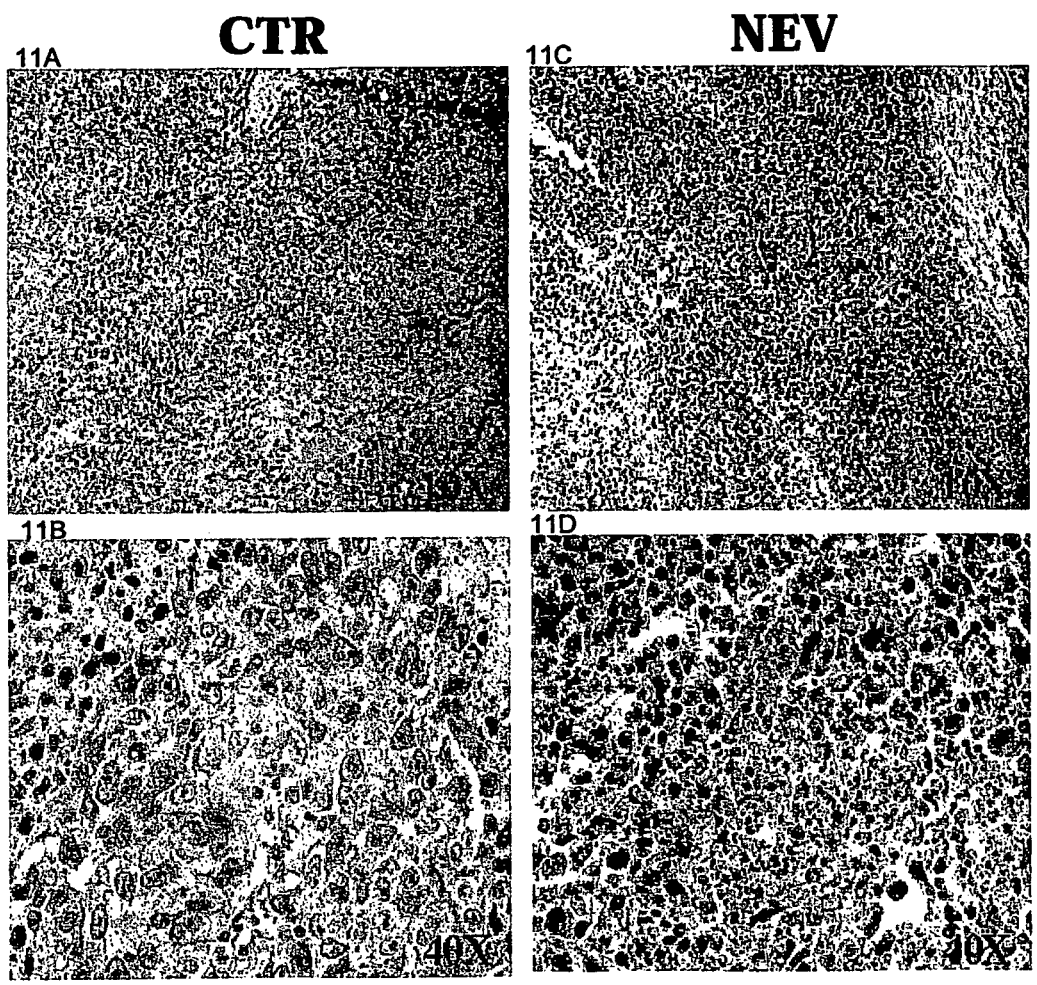
FIG. 11: Tissue samples from nevirapine-treated (panels NEV) and untreated sample (panels CTR) rats. In the upper panels (10× objective), transformed areas in the NEV panel FIG. 11B are remarkably reduced compared to the untreated (CTR) tissue (FIG. 11A). In the lower panels (40× objective), cells undergoing apoptosis are clearly visible in the NEV (FIG. 11D) but not in the CTR sample (FIG. 11C).

Results: After 17 days from inoculation, control rats show typical tumors of 2-4 cm$^3$ whereas only one of the nevirapine pre-treated animals shows a small nodule of a few millimeters in the site of injection. The time curve in FIG. 10 shows the differential rates of tumor growth in control (solid line) and nevirapine-treated rats (broken line). The growth curve of controls represents the average value of the three animals, whereas the nevirapine curve refers to the growth rate of the single animal, among those that were treated, which developed a small-size tumor. Tumor tissues were surgically removed from both non-treated and nevirapine-treated rats and submitted to histological analysis. FIG. 11 shows that in the sample from nevirapine-treated rat (panels NEV) the transformed areas are remarkably reduced, and cells present clear apoptotic features, compared to untreated sample (panels CTR).

In conclusion, pre-treatment with nevirapine effectively antagonize the onset and the growth of an experimentally induced hepatoma in rats (⅔) genetically predisposed to develop that specific tumor. Two rats remained permanently healthy after tumor inoculation, whereas in the third one a small-size tumor is detected. Under the same conditions, untreated rats develop this fast-growing tumor (⅗) and generally die within 27 days.

EXAMPLE 10

Anti-Tumor Activity of Nevirapine in vivo: Treatment of BALB/C Mice Inoculated with Ascite Tumor Procedure: 10 BALB/C mice were inoculated intraperitoneally (twice) with ascite tumor cells by injecting 0.2 ml of ascite withdrawn from an animal inoculated 8 days before. Treatment with nevirapine started on the same day by injecting intraperitoneally 1 mg/mouse/day (stock solution 10 mg/ml in DMSO) in 5 of the 10 mice inoculated with the tumor cells. Mice were treated continuously with nevirapine for seven days.

Results: After 7-8 days, all control animals showed a swollen abdomen containing 5-7 ml of ascite, as determined after the animals were sacrificed. In contrast, three out of five (⅗) nevirapine-treated animals remain healthy with no evidence of tumor growth; the absence of tumor development was confirmed when 2 of these animals were sacrificed 15 days after tumor inoculation and the bodies were analyzed. The surviving treated animal remained permanently healthy. It is worth recalling that mice inoculated with ascite tumor survive only 12-14 days.

In conclusion, this experiment proves that nevirapine, injected at the same time as tumor inoculation, blocks permanently the onset of ascite tumor in three out of five mice. Under the same conditions, the tumor developed in non-treated rats (⁵⁄₅), all of which died 12-14 days after inoculation.

EXAMPLE 11

Figure 12:
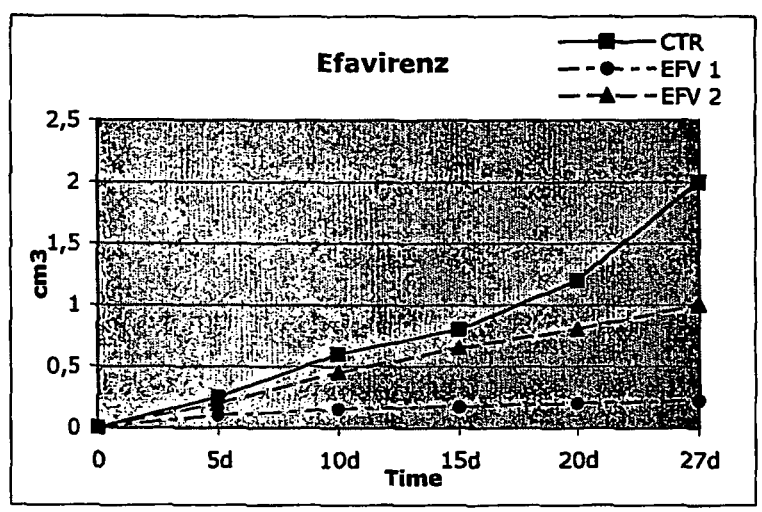
FIG. 12: Morris hepatoma growth in control (solid line) and two efavirenz-treated rats (broken lines, EFV1 and EFV2). The rate of tumor growth is expressed as the volume (in $cm^3$) over time (in days from the time of inoculation).

Anti-Tumor Activity of Efavirenz in vivo: Treatment of Morris 3924A Rat Hevatoma Procedures and Results: Morris hepatoma cells were inoculated in 4 rats (3924A strain). The same day, treatment with efavirenz was initiated in two of them by injecting 1 mg/rat/day. FIG. 12 shows the growth rate of the tumors in control (solid line) and efavirenz-treated animals (broken line). The tumor grew rapidly in control animals, which both died at the 27$^{th}$ day after inoculation; in contrast only one of two treated animals developed a tumor of markedly smaller size, whereas the other remained totally healthy.

In conclusion, this experiment proves that treatment with efavirenz, initiating the same time as tumor inoculation, effectively antagonizes the onset and growth of Morris hepatoma. Of two treated rats, one remained healthy several weeks after is tumor inoculation, while the second one developed a markedly smaller tumor. Under the same conditions, the tumor developed in non-treated rats (²⁄₂) and died at the 27$^{th}$ day.

The invention claimed is:

1. A method to treat a subject comprising the step of administering to a subject identified as having a tumor selected from the group consisting of a carcinoma, a fibrosarcoma and an osteo-sarcoma an effective amount of at least a compound selected from the group consisting of, nevirapine, efavirenz, delavirdine, and corresponding salts of nevirapine, efavirenz, and delavirdine to exhibit an anti-tumor action.

2. The method according to claim 1 wherein the compound reconverts differentiated cells of the tumor into phenotypically normal cells.

3. The method according to claim 1 wherein said carcinomas are selected from the group of teratocarcinoma, colon carcinoma, breast carcinoma, adenocarcinoma, and hepatoma.

4. The method according to claim 1 wherein the compound is present in a pharmaceutical composition that further comprises one or more carriers and/or diluents and/or solvents and/or excipients suitable for oral, intravenous, intramuscular or hypodermic injection administration.

5. The method according to claim 1, wherein the compound is present in a pharmaceutical composition in the form of a pill, suspension, or solution.

* * * * *